US009202272B2

(12) United States Patent
Akcakaya et al.

(10) Patent No.: US 9,202,272 B2
(45) Date of Patent: Dec. 1, 2015

(54) METHOD AND APPARATUS FOR IMAGE ENHANCEMENT IN MAGNETIC RESONANCE IMAGING USING MOTION CORRUPTED DATA

(71) Applicant: Beth Israel Deaconess Medical Center, Inc. (BIDMC, INC.), Boston, MA (US)

(72) Inventors: Mehmet Akcakaya, Cambridge, MA (US); Jaime L Shaw, Los Angeles, CA (US); Reza Nezafat, Newton, MA (US); Sebastien Roujol, Brookline, MA (US)

(73) Assignee: Beth Israel Deaconess Medical Center, Inc. (BIDMC, INC.), Boston, MA (US)

( * ) Notice: Subject to any disclaimer, the term of this patent is extended or adjusted under 35 U.S.C. 154(b) by 340 days.

(21) Appl. No.: 13/690,434

(22) Filed: Nov. 30, 2012

(65) Prior Publication Data

US 2014/0079305 A1 Mar. 20, 2014

Related U.S. Application Data

(60) Provisional application No. 61/703,439, filed on Sep. 20, 2012.

(51) Int. Cl.
*G06K 9/00* (2006.01)
*G06T 7/00* (2006.01)
*G06T 7/20* (2006.01)

(52) U.S. Cl.
CPC ............... *G06T 7/0012* (2013.01); *G06T 7/20* (2013.01); *G06T 2207/10088* (2013.01)

(58) Field of Classification Search
None
See application file for complete search history.

(56) References Cited

U.S. PATENT DOCUMENTS

| 7,545,967 | B1 * | 6/2009 | Prince et al. ................ 382/130 |
| 8,768,034 | B2 * | 7/2014 | Liu et al. .................... 382/131 |
| 2009/0148021 | A1 * | 6/2009 | Yui ............................ 382/131 |
| 2013/0251225 | A1 * | 9/2013 | Liu et al. .................... 382/131 |

OTHER PUBLICATIONS

Scott et al, "Motion in Cardiovascular MR Imaging", Radiology, Feb. 2009.*

* cited by examiner

*Primary Examiner* — Avinash Yentrapati
(74) *Attorney, Agent, or Firm* — Cha & Reiter, LLC (57) ABSTRACT

An apparatus and method process image data, including motion corrupted data, from a magnetic resonance imaging procedure to obtain and reconstruct images for cardiac, cardiovascular, coronary arterial, and/or pulmonary vein diagnoses in a subject. The apparatus and method include a processor operating predetermined software which receives the image data, classifies the received image data as accepted image data or rejected image data, and applies a predetermined relationship between the accepted image data and the rejected image data to correct for motion of the subject and to generate and output a reconstructed image of the subject corrected for the motion from the image data, with the reconstructed image having a relatively high signal-to-noise ratio.

23 Claims, 5 Drawing Sheets

METHOD AND APPARATUS FOR IMAGE ENHANCEMENT IN MAGNETIC RESONANCE IMAGING USING MOTION CORRUPTED DATA

This application claims the benefit of U.S. Provisional Application Ser. No. 61/703,439 filed Sep. 20, 2012, the teachings of which are incorporated herein by reference.

BACKGROUND OF THE INVENTION

1. Field of the Invention

The present invention relates to magnetic resonance imaging (MRI), and in particular to image enhancement in MRI using motion corrupted data.

2. Description of the Related Art

Methods are known in the prior art for obtaining and reconstructing images from MRI scanning, with various advantages and disadvantages in image processing for specific diagnostic goals. For example, three-dimensional (3D) high-resolution cardiac MRI (CMR), such as coronary MRI and late gadolinium enhancement (LGE) imaging, as well as MR angiography (MRA), is acquired in a segmented fashion over multiple heartbeats, which necessitates compensation of respiratory and cardiac motions. The latter is typically suppressed by imaging during the patient-specific rest period of the cardiac cycle. For high-resolution 3D sequences, when the acquisition cannot be completed within a single breath-hold, techniques for respiratory motion compensation have been developed.

For example, the respiratory navigator (NAV) is a known technique or method, in which a navigator echo is acquired to measure the displacement of the right hemi-diaphragm (RHD) during scanning. This displacement measurement is then used to determine whether or not the acquired imaging data should be retained for image reconstruction. For example, some NAV methods utilize a two-dimensional (2D) pencil beam typically positioned on the dome of the right hemi-diaphragm, and have been used to track respiratory motion. Due to a linear dependency between the respiratory motion of the heart and that of the RHD, NAV can be used to indirectly monitor the motion of the heart. In prospective NAV gating, the k-space lines, obtained from the k-space of MRI data, and which are acquired immediately after the navigator signal, are used for image reconstruction only if the NAV signal is within a pre-defined gating window.

Otherwise, the corresponding k-space lines outside the pre-defined gating window are rejected for possibly being motion-corrupted due to respiratory and/or cardiac motion, and thus such k-space lines would reduce image quality if included and processed during image reconstruction. Subsequently, new k-space lines are re-acquired in the next cardiac cycle. For a 5 mm. gating window, this typically results in an acceptance efficiency of 30-70%, in which the rejected lines are discarded and not used in the image reconstruction.

Alternative techniques have been developed to improve the efficiency of respiratory motion compensation. Prospective motion correction has been utilized in coronary MRI to achieve scan efficiencies of 80-100%. Retrospective motion estimation has also been used in coronary MRI to correct for the motion of the rejected lines for 3D radial trajectories with projection-based self-gating, and for sequences using image-based navigators. Self-gating with radial trajectories has been employed in LGE imaging as well, but image-based navigators may not be directly applicable in this case due to the inversion pulse applied prior to imaging.

Another major challenge in high-resolution cardiac MRI is the limited signal-to-noise ratio (SNR). In coronary MRI, administration of vasodilators, imaging at higher magnetic field strengths, and the use of exogenous contrast agents have been investigated as ways of improving the SNR for reconstructing images. In LGE imaging, the limited SNR can be improved by imaging over alternate heartbeats, thereby allowing more signal re-growth, although this approach also doubles the scan time. For 2D LGE imaging with breath-hold acquisitions, motion-corrected averaging has been utilized. However, due to long acquisition times and inter-average motion, multiple averages for 3D imaging are rarely used.

An improved image reconstruction method with a higher SNR would be advantageous in MRI applications to cardiac and cardiovascular diagnoses.

SUMMARY OF THE INVENTION

An apparatus and method process image data, including motion corrupted data, from a magnetic resonance imaging procedure to obtain and reconstruct images for cardiac, cardiovascular, coronary arterial, and/or pulmonary vein diagnoses in a subject. The apparatus and method include a processor operating predetermined software which receives the image data, classifies the received image data as accepted image data or rejected image data, and applies a predetermined relationship between the accepted image data and the rejected image data to correct for motion of the subject and to generate and output a reconstructed image of the subject corrected for the motion from the image data, with the reconstructed image having a relatively high signal-to-noise ratio.

BRIEF DESCRIPTION OF THE DRAWINGS

The above features and advantages of the invention will become more apparent from the following description taken in conjunction with the accompanying drawings in which.

DETAILED DESCRIPTION OF THE INVENTION

Hereinafter, preferred embodiments of the present invention will be described with reference to the accompanying drawings. In the following description, a detailed explanation of known related functions and constructions may be omitted to avoid unnecessarily obscuring the subject matter of the present invention. This invention may, however, be embodied in many different forms and should not be construed as limited to the exemplary embodiments set forth herein. The same reference numbers are used throughout the drawings to refer to the same or like parts. Also, terms described herein, which are defined considering the functions of the present invention, may be implemented differently depending on user and operator's intention and practice. Therefore, the terms should be understood on the basis of the disclosure throughout the same specification. The principles and features of this invention may be employed in varied and numerous embodiments without departing from the scope of the invention.

Furthermore, although the drawings represent exemplary embodiments of the invention, the drawings are not necessarily to scale and certain features may be exaggerated or omitted in order to more clearly illustrate and explain the present invention.

Figure 1:
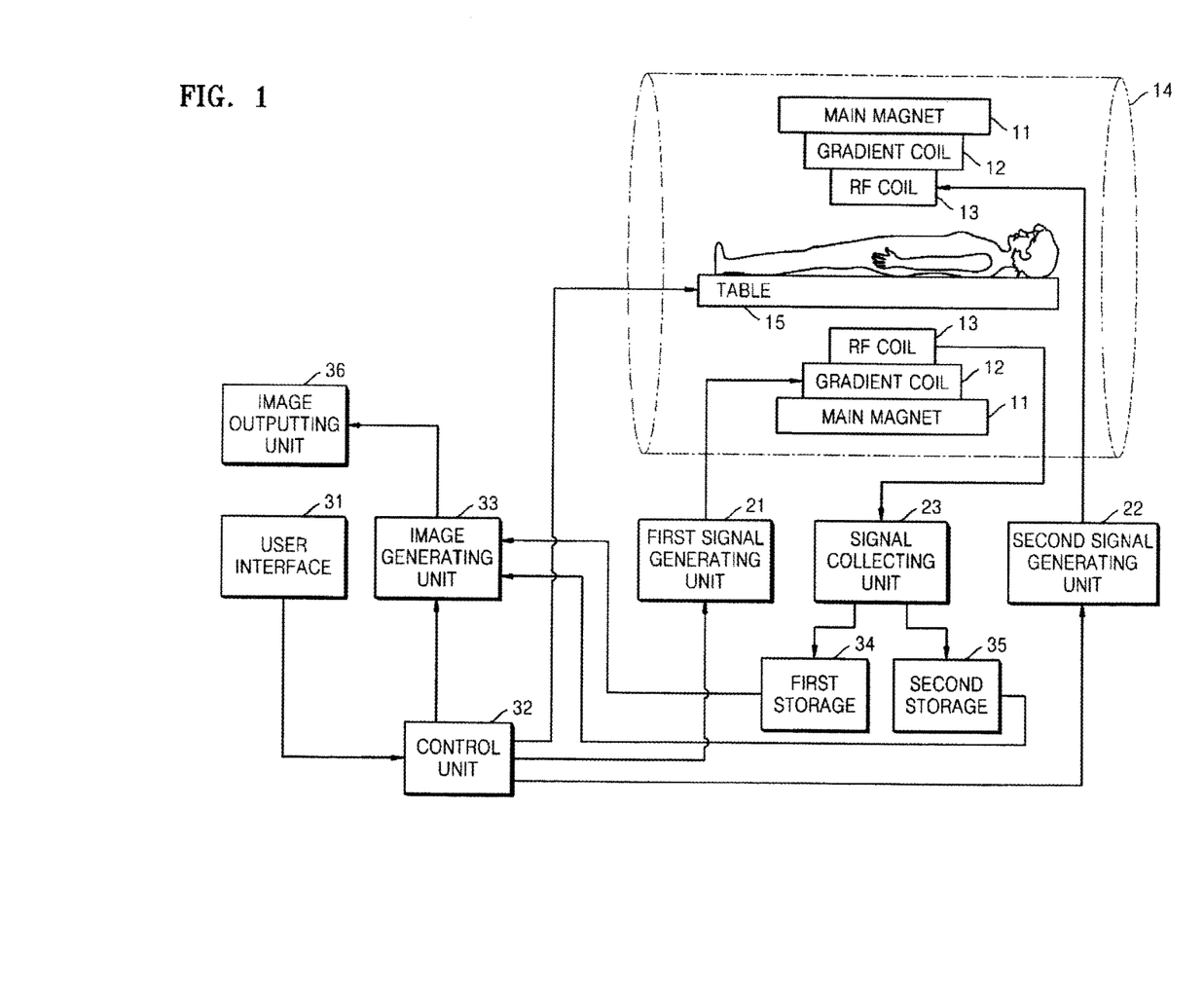
FIG. 1 is a diagram of a structure of a magnetic resonance imaging (MRI) apparatus according to an exemplary embodiment of the present invention.

FIG. 1 is a view illustrating a structure of a magnetic resonance imaging (MRI) apparatus or system according to an exemplary embodiment of the present invention, for generating or reconstructing images from MRI data with image enhancement using motion corrupted data.

Referring to FIG. 1, the MRI apparatus may include a main magnet 11, a gradient coil 12, a radio frequency (RF) coil 13, a shield 14, a table 15, a first signal generating unit 21, a second signal generating unit 22, a signal collecting unit 23, a user interface 31, a control unit 32, an image generating unit 33, a first storage 34, a second storage 35, and an image outputting unit 36. The main magnet 11, the gradient coil 12, and the RF coil 13 are elements for generating a magnetic field to induce magnetic resonance signals from atomic nuclei inside a human body, and may be implemented as a magnet, coils, etc. The shield 14 blocks an electromagnetic wave generated by the RF coil 13 from being radiated to the outside. A target object, for example, a patient, lies on the table 15 inside the shield 14, and the table 15 may move by control of the control unit 32 to move in or out of the assembly of components 11-14, to position the patient for MRI photography.

The first signal generating unit 21, the second signal generating unit 22, and the signal collecting unit 23 are components for transmitting signals to generate the magnetic field in the gradient coil 12 and the RF coil 13 by the control of the control unit 32 or for collecting signals received in the RF coil 13 and providing the image generating unit 13 with the collected signals, and may be implemented as an oscillator, an amplifier, a modulator, a demodulator, an analog-to-digital converter (ADC), a digital-to-analog converter (DAC), etc. The user interface 31, the control unit 32, the image generating unit 33, the first storage 34, the second storage 35, and the image outputting unit 36 are components for controlling the first signal generating unit 21 and the second signal generating unit 22 or for processing signals collected by the signal collecting unit 23, and may be implemented as a computer and peripheral devices of the computer.

The main magnet 11 generates a static magnetic field for arranging directions of magnetic dipole moments of atomic nuclei, typically hydrogen nuclei in water molecules, inside the human body in one direction. Examples of the main magnet 11 for generating the static magnetic field include a permanent magnet, a room temperature electromagnet, a superconductivity electromagnet, etc. A magnetic field generated by the superconductivity electromagnet is strong and uniform, and thus the superconductivity electromagnet is mainly used as the main magnet 11. For example, if hydrogen atomic nuclei inside the human body are placed in the static magnetic field generated by the main magnet 11, directions of magnetic dipole moments of the hydrogen atomic nuclei are arranged in a direction of the static magnetic field generated by the main magnet 11 in order to go into a lower energy state. To maintain a thermal parallel state, the number of atomic nuclei in a low energy state is actually slightly greater than the number of atomic nuclei in a high energy state. In this regard, an energy difference between atomic nuclei in different energy states is proportional to an intensity of the static magnetic field generated by the main magnet 11, and has an intrinsic Larmor frequency associated with Larmor precession of the atomic nuclei. For example, if the intensity of the static magnetic field generated by the main magnet 11 is 1 Tesla, the Larmor frequency of a hydrogen atomic nucleus in the static magnetic field generated by the main magnet 11 is 42.58 MHz, and the Larmor frequency of a sodium atomic nucleus therein is 11.27 MHz.

The gradient coil 12 generates a gradient magnetic field that varies at a constant gradient with respect to each of a plurality of directions, for example, directions x, y, and z, in proportion to a distance from a reference location within the static magnetic field generated by the main magnet 11. In this regard, the reference location may be an origin point of a 3D coordinate system when a space including a static magnetic field generated by the main magnet 11 is presented as the 3D coordinate system. Each of the magnetic resonance signals received by the RF coil 13 has location information in a 3D space due to the gradient magnetic field generated by the gradient coil 12. The gradient coil 12 may comprise an X gradient coil for generating the gradient magnetic field that varies in the direction x, a Y gradient coil for generating the gradient magnetic field that varies in the direction y, and a Z gradient coil for generating the gradient magnetic field that varies in the direction z.

The RF coil 13 generates an electromagnetic wave signal having an RF corresponding to a type of an atomic nucleus, i.e., an RF signal, and applies the electromagnetic wave signal to the target object in order to transit the atomic nucleus from the low energy state to the high energy state. Atomic nuclei inside the target object are excited by the applied electromagnetic wave signal. In this regard, the target object is generally an MR image captured site of the human body, or may be a living body other than the human body or an inanimate object. For example, the RF coil 13 may generate the electromagnetic wave of 42.58 MHz to transit an energy state of the hydrogen atomic nucleus within the static magnetic field of 1 Tesla. Also, the RF coil 13 may generate the electromagnetic wave of 11.27 MHz to transit an energy state of the sodium atomic nucleus within the static magnetic field of 1 Tesla. If the electromagnetic wave signal generated by the RF coil 13 is applied to an atomic nucleus, the atomic nucleus is transited from a low energy state to a high energy state. Thereafter, if the electromagnetic wave signal generated by the RF coil 13 disappears, i.e. if the electromagnetic wave applied to the atomic nucleus disappears, the atomic nucleus radiates an electromagnetic wave having the same Larmor frequency while being transited from the high energy state to the low energy state.

The RF coil 13 receives an electromagnetic wave signal radiated from atomic nuclei inside the target object. The electromagnetic wave signal is referred to as a free induction decay (FID) signal. The FID signal is referred to as an echo signal with respect to the electromagnetic wave signal applied to the target object as a magnetic resonance signal used to generate a magnetic resonance image. A length of a time interval from a time point when the electromagnetic wave signal is applied to the target object, i.e. a time point when the electromagnetic wave signal is generated, to a time point when the electromagnetic wave signal is received from the target object is referred to as an echo time (TE). A length of a time interval when an application of the electromagnetic wave signal to the human body repeats is referred to as a repetition time (TR).

The RF coil 13 may be implemented as one coil having a function of generating an electromagnetic wave having an RF corresponding to a type of an atomic nucleus and a function of receiving an electromagnetic wave radiated from the atomic nucleus, or may be implemented as a transmission coil having the function of generating the electromagnetic wave having the RF corresponding to the type of the atomic nucleus and a reception coil having the function of receiving the electromagnetic wave radiated from the atomic nucleus. In particular, according to the present embodiment of FIG. 1, the reception coil of the RF coil 13 may be implemented as a dual tuned coil capable of receiving several frequencies in one coil, may be implemented as a multi-channel coil capable of simultaneously receiving a plurality of magnetic resonance signals, or may be implemented as a dual tuned multi-channel coil.

The user interface 31 receives a command from an operator of the MRI apparatus of FIG. 1 and outputs the command to the control unit 32. The user interface 31 may be implemented as a general input device of a computer, such as a keyboard and a mouse. The image outputting unit 36 outputs the magnetic resonance image generated by the image generating unit 33. The image outputting unit 36 may be implemented as a general output device of the computer such as a monitor. The control unit 32 controls the first signal generating unit 21, the second signal generating unit 22, the signal collecting unit 23, and the image generating unit 33 according to the command output from the user interface 31. The image generating unit 33 generates a magnetic resonance image by using magnetic resonance signals that are collected by the signal collecting unit 23 and are stored in the first storage 34 and the second storage 35. The control unit 32 and the image generating unit 33 may be implemented as a high performance computer capable of promptly processing a large amount of data required to generate the magnetic resonance image. Meanwhile, it will be understood by one of ordinary skill in the art that the terms "generating the magnetic resonance image" may be replaced by various terms such as reconstructing the magnetic resonance image.

The control unit 32 generates a control signal indicating an alternating signal having a frequency varying at a certain gradient with respect to each of the directions x, y, and z, and outputs the control signal to the second signal generating unit 22. The first signal generating unit 21 generates the alternating signal having a frequency varying at a constant gradient with respect to each of the directions x, y, and z according to the control signal received from the control unit 32, and outputs the alternating signal to the gradient coil 12. The gradient coil 12 generates a gradient magnetic field that varies at a constant gradient with respect to each of the directions x, y, and z according to the alternating signal received from the first signal generating unit 21. The control unit 32 generates a control signal indicating a pulse train, and outputs the control signal to the second signal generating unit 22. The second signal generating unit 22 generates an alternating signal having the pulse train according to the control signal received from the control unit 32, and outputs the alternating signal to the RF coil 13. The RF coil 13 generates an electromagnetic wave signal having the pulse train according to the alternating signal received from the second signal generating unit 22. The first signal generating unit 21 and the second signal generating unit 22 may be implemented as ADCs for converting analog signals received from the control unit 32 into digital signals, oscillators for generating source signals, modulators for modulating the source signals according to signals received from the control unit 32, amplifiers for amplifying the signals modulated by the modulators, etc. Such amplified signals are sent to the coils 12, 13.

The signal collecting unit 23 collects magnetic resonance signals induced by atomic nuclei through the RF coil 13. The signal collecting unit 23 may be implemented as an amplifier for amplifying magnetic resonance signals received from the RF coil 13, a demodulator for demodulating the magnetic resonance signals amplified by the amplifier, a DAC for converting analog magnetic resonance signals demodulated by the demodulator into digital magnetic resonance signals, etc. The magnetic resonance signals converted into digital form are separately stored as acquired MRI data in the first storage 34 and the second storage 35. The first storage 34 and the second storage 35 are not necessarily physically separated storages but are spaces for separately storing different types of magnetic resonance signals. For example, the first storage 34 and the second storage 35 may be different storage regions of a hard disk. Alternatively, the first storage 34 and the second storage 35 may be combined and implemented by a single storage unit.

The RF coil 13 generates an electromagnetic wave from an alternating current applied from the second signal generating unit 22 to the RF coil 13, and receives an electromagnetic wave by a collection of signals by the signal collecting unit 23, and thus it is possible to freely adjust a time when the RF coil 13 generates a pulse and a time when the RF coil 13 receives the pulse.

In a preferred embodiment shown in FIG. 1, the image generating unit 33 performs the method for generating or reconstructing images from the acquired MRI data with image enhancement using motion corrupted data as described herein with reference to FIGS. 3-7.

Figure 2:
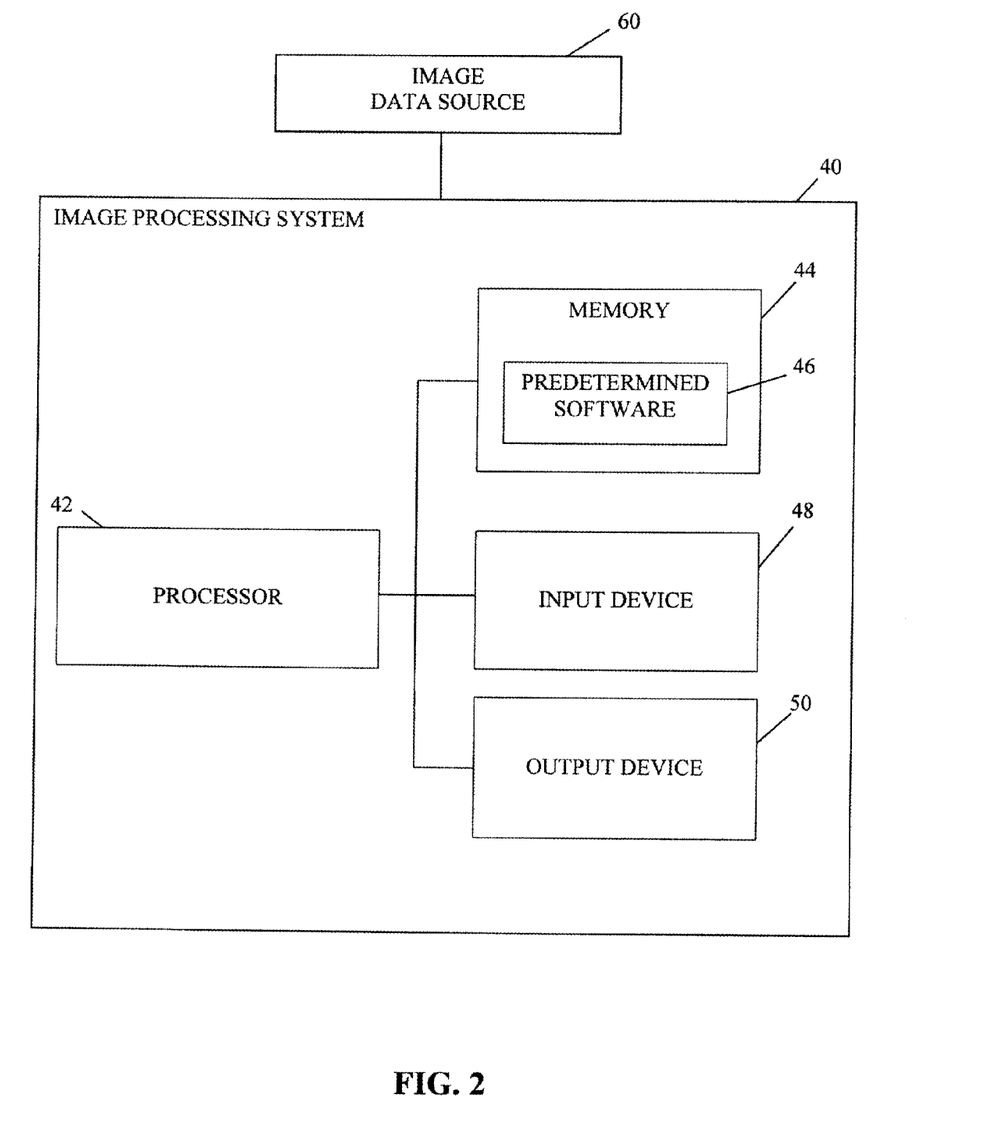
FIG. 2 is a block diagram illustrating an image processing system in accordance with an alternative exemplary embodiment of the present invention.

Referring to FIG. 2, in an alternative exemplary embodiment of the present invention, the apparatus performs the method for generating or reconstructing images from the MRI data with image enhancement using motion corrupted data as described herein with reference to FIGS. 3-7, and includes an image processing system 40 having a processor 42, a memory 44 for storing data and operational programs such as predetermined software 46, an input device 48, and an output device 50. The output device 50 may include the image outputting unit 36 of FIG. 1, which may be a display, a printer, etc. for displaying reconstructed MR images, or the output device 50 may be a communications interface for connecting to the image outputting unit 36. The input device 48 may include a keyboard and/or a mouse for receiving user inputs and selections, and may incorporate or be connected to the user interface 31 of FIG. 1. In addition, the input device 48 and the output device 50 may operate together to be a graphic user interface (GUI), for example, provided to the user of the MRI apparatus by the user interface 31 in a manner known in the art. In alternative embodiments, the input device 48 and the output device 50 may include a touch screen to provide the GUI which responds to user touches, in a manner known in the art, for operating the image processing system 40 of the present invention.

In the alternative exemplary embodiment of FIG. 2, the image processing system 40 is a stand-alone computer, and the image reconstruction may be performed off-line; that is, independent of the image acquisition process of, for example, the MRI system of FIG. 1. Alternatively, the image reconstruction may be performed contemporaneously with the acquisition of images of a subject by the MRI system of FIG. 1.

Figure 3:
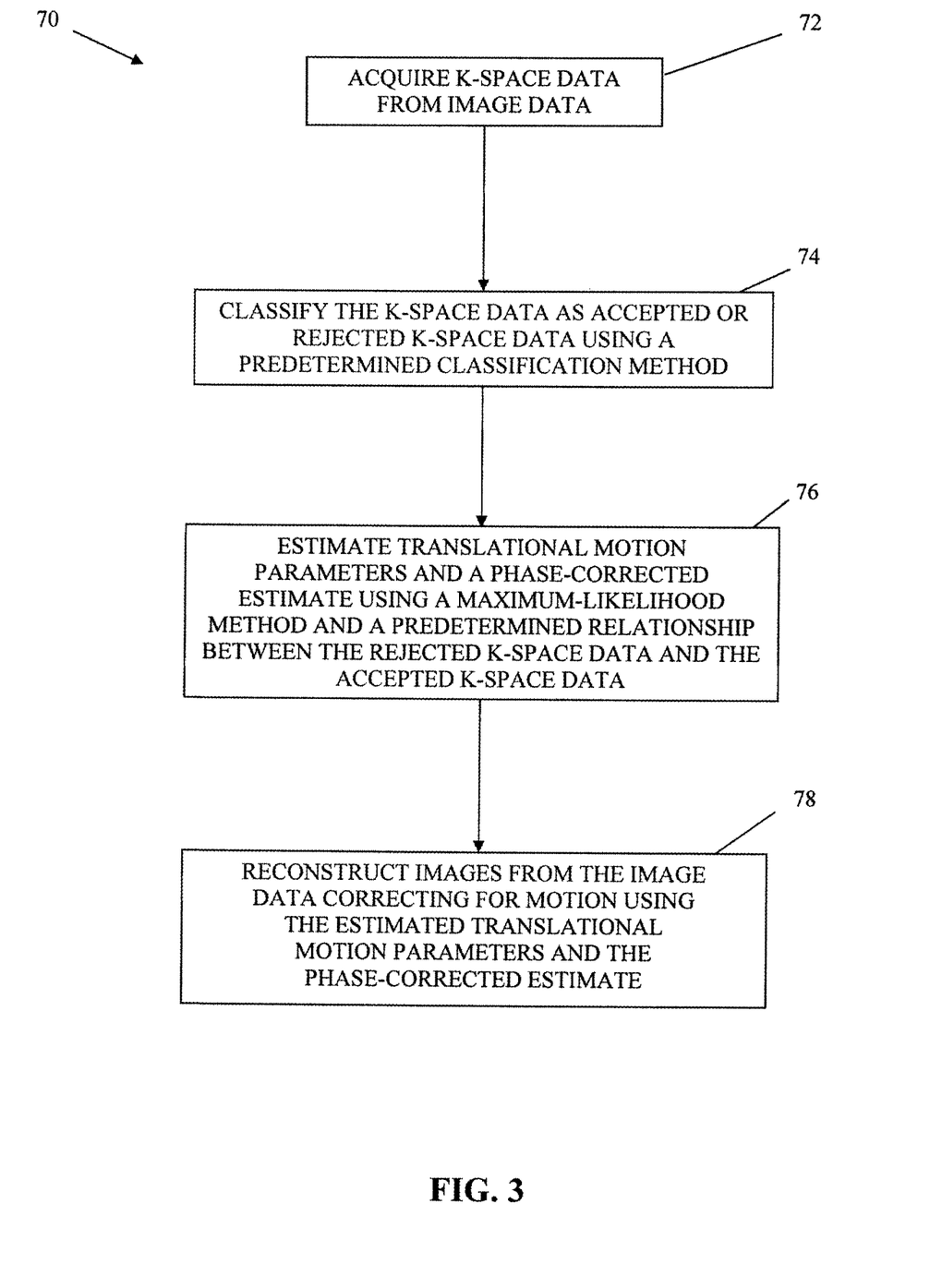
FIG. 3 is a flow chart of a method of operation of the exemplary embodiment of the present invention.

The image reconstruction is performed using customized software, as the predetermined software 46 implementing the method 70 described herein in conjunction with FIG. 3, and such predetermined software 46 may be generated using mathematical software development and authoring tools, such as MATLAB v7.6, a mathematical and numerical computing environment implemented as a software application commercially available from MATHWORKS, Natick, Mass., U.S.A. Alternatively, the predetermined software 46 may be implemented by any known programming language or environment, for example, by using the C++ programming language.

The image processing system 40 receives and processes image data from an image data source 60, with the received image data stored in the memory 44. The image data source 60 may include the entire MRI apparatus of FIG. 1, which may be implemented using, for example, a 1.5 T ACHIEVA magnet as the main magnet 11, commercially available from PHILIPS HEALTHCARE, of Best, The Netherlands, which has a 5-channel coil for performing cardiac MRI measurements on the cardiac region of a subject, such as a patient, and alternatively capable of being upgraded to a 32-channel cardiac phased-array receiver coil. In the alternative exemplary embodiment of FIG. 2, the image data source 60 is operatively connected by a wired and/or wireless connection to the image processing system 40. The image data source 60 may also be embodied as one or both of the first storage 34 and the second storage 35 in FIG. 1 for receiving and storing data corresponding to RF signals, MR signals, and other known data signals from the respective coils 12, 13.

In further alternative embodiments, the image processing system 40 is connected, using a wired and/or wireless connection, to a computer network, such as the Internet, and receives the image data from at least one or even multiple remote sources, such as medical image data archives as the image data source 60. For example, the MRI images collected by a hospital or other MRI facilities, for example, using the apparatus of FIG. 1 or other known MRI apparatus, may store the images in a storage facility as the image data source 60, which may be remotely accessed by the image processing system 40 of the present invention using known communication devices and methods.

Referring to FIGS. 2-3, the predetermined software 46 implements a method 70 for performing image reconstruction from the image data received from the image data source 60. The method includes the steps of acquiring k-space data from image data in step 72; classifying the k-space data as accepted or rejected k-space data using a predetermined classification method in step 74; iteratively estimating translational motion parameters and a phase-corrected estimate using a maximum-likelihood method and a predetermined relationship between the rejected k-space data and the accepted k-space data in step 76; and reconstructing images from the image data correcting for motion using the estimated translational motion parameters and the phase-corrected estimate in step 78.

Referring to FIGS. 1-3 in greater detail, the present invention is a method for utilizing the k-space data corresponding to motion distorted or corrupted data, which is typically rejected by respiratory navigators in the prior art, with the present invention providing an improved signal-to-noise ratio when reconstructing MR images. Respiratory motion is compensated for by using respiratory navigators, which track the motion of nearby organs, such as motion of a right-hemi-diaphragm for imaging the heart, and if the motion detected by the navigator is within a pre-defined window, the data is classified as accepted data in step 74; otherwise such data is classified as rejected data in step 74. However, in the present invention, such rejected data is not discarded by the present invention, as would be the case in the prior art. Instead, the present invention utilizes these rejected data, such as lines of k-space data, referred to herein as "k-space lines", instead of discarding such k-space lines as is done by methods in the prior art.

In combination with a respiratory motion correction method based on maximum-likelihood estimation, these rejected k-space lines are used in the present invention to compensate for motion of the object with the accepted k-space lines to improve the signal-to-noise ratio (SNR) without increasing or prolonging the scan and data acquisition time. That is, since such rejected k-space lines are obtained during the ordinary scanning process along with the accepted k-space lines, the apparatus and method of the present invention do not require any additional scan or data acquisition time to obtain the MR image data which includes image reconstruction using the rejected k-space lines.

In general, for an image of an object, such as a patient or subject, as shown, for example, positioned in the MRI apparatus in FIG. 1, the image is represented by a vector m(x,y,z) and has a corresponding k-space represented by a vector $S(k_x, k_y, k_z)$. When the object undergoes a translational motion of $(x_0, y_0, z_0)$, the k-space experiences a phase-shift as shown in Equation 1:

$$\hat{\vec{s}}(k_x,k_y,k_z) = e^{-i2\pi k_x x_0 - i2\pi k_y y_0 - i2\pi k_z z_0} \vec{S}(k_x,k_y,k_z). \quad (1)$$

For a navigator-gated segmented imaging protocol, a k-space line at $(k^o_y, k^o_z)$ is to be acquired. Thus, as described herein, the k-space line has a dependency on $(k^o_y, k^o_z)$, which is to be understood in the following description. This k-space line is rejected and/or classified as rejected k-space data in step 74 if the NAV detects that the object has moved, and so the NAV classifies this k-space line as corrupted by the motion of the object. In this case, the rejected k-space line is given by Equation 2:

$$\vec{S}^{rej,1} = e^{-i2\pi k_x x_1 - i2\pi k_y y_1 - i2\pi k_z z_1} \vec{S}_0 + \vec{n} \quad (2)$$

in which s is the vector of values along the read-out $(k_g)$ direction corresponding to the original image m(x,y,z), $s^{rej,1}$ is the first rejected k-space line at this k-space location, $n_1$ is the measurement noise, $(x_1, y_1, z_1)$ are the new translational values of the object, based on the first rejected k-space line, $k_x$ is the vector of values of the k-space extending in the read-out direction, and o denotes element-wise multiplication of vector components. If a currently acquired k-space line is rejected by NAV, a new k-space line is then re-acquired, evaluated by NAV, and either accepted or rejected, and this acceptance-or-rejection process using NAV is repeated until an acceptable k-space line is within an acceptable gating window.

The k-space line, corresponding to the $p^{TH}$ time that such a k-space line is rejected, is defined as in Equation 3:

$$\vec{S}^{rej,p} = e^{-i2\pi k_x x_p - i2\pi k_y y_p - i2\pi k_z z_p} \vec{S}_0 + \vec{n}_p. \quad (3)$$

Since the vectors s along the read-out $k_x$ direction only contains measurements along the $k_x$ direction for a fixed $(k^o_y, k^o_z)$ location, the motion in the y-z plane cannot be determined individually. Thus, the rejected k-space line can be re-written as in Equation 4:

$$\vec{S}^{rej,p} = e^{-i2\pi k_x x_p - i\theta_p} \vec{S}_0 + \vec{n}_p, \quad (4)$$

with $\theta_p$ being a translational motion parameter in the y-z plane for the $p^{TH}$ rejected line, and $s^{rej,p}$ is the phase parameter for the $p^{TH}$ rejected line, thus reducing the number of unknowns. Similarly, the accepted line is given by Equation 5:

$$\vec{s}^{acc} = \vec{s} + \vec{n}_{acc}. \qquad (5)$$

Image reconstruction using methods in the prior art is performed by filling the k-space, $S(k_x, k_y, k_z)$, with only the accepted lines $s^{acc}$ for each k-space location $(k^0_y, k^0_z)$. However, one goal of the present invention is to reduce the effect of the noise by using all of the available k-space lines, including the rejected k-space lines not hitherto used but instead discarded in the prior art.

The present invention utilizes a 3D translational motion model, which was successfully used in previous high-resolution cardiac MRI studies to reduce motion artifacts, and has been shown to be the dominant component of affine motion models. Such a 3D translational motion model has been used and described in Keegan J, Gatehouse P D, Yang G Z, Firmin D N, "Non-model-based correction of respiratory motion using beat-to-beat 3D spiral fat-selective imaging", J. Magn Reson Imaging 2007; 26(3): pp. 624-629. Using such a 3D translational motion model, the maximum likelihood (ML) estimates of the motion parameters and the k-space line are jointly determined from the corresponding accepted and rejected k-space lines.

Under an independent identically distributed Gaussian noise assumption, the likelihood function for the unknown variables s and $$\{x_p, \theta_p\}_{p=1}^{n_{rej}}$$

can be written as Equation 6:

$$L(\vec{s}, \{x_p, \theta_p\}_{p=1}^{n_{rej}}) = -\|\vec{s} - \vec{s}^{acc}\|_2^2 - \sum_{p=1}^{n_{rej}} \|\vec{s}^{rej,p} - e^{-i2\pi k_x x_p - i\theta_p} \cdot \vec{s}\|_2^2, \qquad (6)$$

in which $n_{rej}$ is the number of NAV-rejected lines at the given k-space location, with each $x_p$ and $\theta_p$ being the translational motion parameters, and $s^{rej,p}$ being the phase parameter for the $p^{TH}$ rejected line. The maximum-likelihood estimate is then given by Equation 7:

$$(\vec{s}^{ML}, \{x_p^{ML}, \theta_p^{ML}\}_{p=1}^{n_{rej}}) = \qquad (7)$$

$$\arg\min_{\vec{s}, \{x_p, \theta_p\}_{p=1}^{n_{rej}}} \|\vec{s} - \vec{s}^{acc}\|_2^2 + \sum_{p=1}^{n_{rej}} \|\vec{s}^{rej,p} - e^{-i2\pi k_x x_p - i\theta_p} \cdot \vec{s}\|_2^2$$

which sets forth a predetermined relationship between the accepted k-space lines and the rejected k-space lines.

In an exemplary embodiment of the present invention, an alternating minimization method known in the art is performed to obtain the model parameters $x_p$ and $\theta_p$ from Equation 7 associated with the maximum-likelihood estimate using non-linear least squares methods. Such an alternating minimization method is described in Lee D D, Seung H S, "Algorithms for non-negative matrix factorization", 2001 December. Proceedings Adv. Neural Inform. Process. Systems, pp. 556-562; and Berry M W, Browne M, Langville A N, Pauca V P, Plemmons R J, "Algorithms and applications for approximate nonnegative matrix factorization", Comp Stat Data Analysis 2007; 52(1): pp. 155-173. However, it is to be understood that other known methods, such as gradient descent or Newton's method of approximation, also known as the Newton-Raphson method, may also be used to obtain the model parameters $x_p$ and $\theta_p$ from Equation 7.

Accordingly, in the exemplary embodiment of the present invention using the alternating minimization method, at each iteration t, a current estimate $s^{(t)}$ is held fixed, and for each p, the relation according to Equation 8:

$$(x_p^{(t)}, \theta_p^{(t)}) = \arg\min_{x_p, \theta_p} \|\vec{s}^{rej,p} - e^{-i2\pi k_x x_p - i\theta_p} \cdot \vec{s}^{(t)}\|_2^2 \qquad (8)$$

is solved for the model parameters $x_p$ and $\theta_p$. Then, $$\{x_p^{(t)}, \theta_p^{(t)}\}_{p=1}^{n_{rej}} \qquad (9)$$

is held fixed, and $s^{(t+1)}$ is generated as follows, in Equation 10:

$$\vec{s}^{(t+1)} = \arg\min_{\vec{s}} \|\vec{s} - \vec{s}^{acc}\|_2^2 + \sum_{p=1}^{n_{rej}} \|\vec{s}^{rej,p} - e^{-i2\pi k_x x_p - i\theta_p} \cdot \vec{s}\|_2^2 \qquad (10)$$

$$= \frac{1}{n_{rej}+1}\left(\vec{s}^{acc} + \sum_{p=1}^{n_{rej}} e^{i2\pi k_x x_p + i\theta_p} \cdot \vec{s}^{rej,p}\right).$$

Finally, in general, for two arbitrary vectors u, v:

$$\hat{\theta} = \arg\min_{\theta} \|\vec{v} - e^{i\theta}\vec{u}\|_2^2 = \angle(\vec{u} * \vec{v}). \qquad (11)$$

Thus, to solve Equation 8, first, the potential displacements $x_j$ are quantized between predetermined values $x_{min}$ and $x_{max}$ with a predetermined step size $x_{step}$. Then, for each value of the displacement $x_j$ in the data set, the corresponding y-z translational motion parameter $\theta_j$ is calculated as:

$$\theta_j = \angle((e^{-i2\pi k_x x_j} \vec{s}^{rej,p}) * \vec{s}^{(t)}). \qquad (12)$$

Then Equation 8 is minimized over the set of parameters for $x_p$ to iteratively obtain the values of the maximum-likelihood estimate, that is, the values of:

$$\vec{s}^{ML}, \{x_p^{ML}, \theta_p^{ML}\}_{p=1}^{n_{rej}} \qquad (13)$$

This approach reduces the search space to only the x direction, and avoids quantization for the y-z translational motion parameter $\theta$.

Accordingly, each $x_p^{ML}$ and $\theta_p^{ML}$ being the translational motion parameters, and $s^{ML}$ being the phase-corrected estimate parameter, are determined which are used to reconstruct the MR image from the entire k-space, including both the accepted and rejected k-space lines, in a manner known in the art. Therefore, using the translational motion parameters and the phase-corrected estimate parameter and the entire k-space, this MR image reconstruction method of the present invention compensates for motion of the object by utilizing the rejected k-space lines using the predetermined relationship between the accepted k-space lines and the rejected k-space lines as shown in Equation 7.

For example, the image reconstruction may be performed using the entire k-space, the translational motion parameters, and the phase-corrected estimate parameter by calculating a root-sum-squares of the individual coil images, by coil sensitivity estimation methods, or by other image reconstruction methods and techniques known in the art.

During implementation of the apparatus and method 70 of the present invention, image reconstruction using the present invention was compared to image reconstruction using the prior art, as shown in FIGS. 4-7, with the present invention and prior art methods being evaluated in-vivo, using coronary MRI and LGE imaging of the left atrium.

To evaluate the present invention compared to the prior art, late gadolinium enhancement LGE) images of the left atrium were acquired in twenty-one patients with atrial fibrillation pre-pulmonary or post-pulmonary vein isolation. Images reconstructed with the present invention and with the methods of the prior art were compared in terms of SNR, and using subjective image quality on a 4-point scale.

For coronary MRI, there was a significant improvement in SNR by the method of the prior art, with an SNR of 42.7±10.6 vs. 36.6÷10.2 in the prior art, and with P<0.001. For LGE, there was a significant increase in SNR of the present invention, with an SNR of 27.9±14.2 vs. 22.7±11.1 in the prior art, and with P<0.001.

All imaging for FIGS. 4-7 was performed using a 1.5 T ACHIEVA magnet as the main magnet 11, commercially available from PHILIPS HEALTHCARE, of Best, The Netherlands, with a 32-channel cardiac phased-array receiver coil.

Ten healthy adult subjects, including eight females, aged 26.6±9.8 years, without contraindications to MRI, were recruited for left anterior descending (LAD) coronary artery imaging. Scout images were acquired with a steady-state free precession (SSFP) sequence with an in-plane resolution of 3.1×3.1 mm$^2$ and a 10 mm. slice thickness. This was followed by an image set acquired with an axial breath-hold cine SSFP sequence having TR/TE=3.7/1.85 ms.; a temporal resolution of 48 ms.; a spatial resolution of 1.7×1.7 mm$^2$; and an acceleration rate of two, which were used to visually identify the quiescent period of the LAD. The corresponding trigger delay was used for coronary acquisition. A low-resolution coronary survey 3D volume was then acquired for localization and assignment of the appropriate imaging slab. A free-breathing electrocardiogram (ECG)-triggered navigator-gated SSFP sequence was used for acquisition. The imaging parameters were TR/TE=4.3/2.1 ms., a flip angle=90°, a field of view=270×270×30 mm$^3$, and a spatial resolution=1.0×1.0× 3.0 mm$^3$. A spectrally-selective fat-saturation sequence and T2 magnetization preparation were used to improve contrast. A navigator placed on the dome of the RHD was used for respiratory motion compensation, utilizing prospective real-time correction with a 5 mm end-expiration gating window and a 0.6 superior-inferior tracking ratio. All images were acquired axially with right-left phase encoding. Saturation bands were placed over the stationary tissues to reduce artifacts along the phase encode direction.

In addition, twenty-one patients, including eight females, aged 60.8±8.6 years, referred for assessment of LA anatomy prior to or post-pulmonary vein isolation (PVI), were recruited for LA LGE imaging. All patients had a history of atrial fibrillation and no contraindications to MRI. Sixteen patients were imaged prior to PVI, and five patients were imaged post-PVI. All subjects were in sinus rhythm. LGE images were acquired 10-to-20 minutes after a bolus (2 ml/s) infusion of 0.1 mmol/kg of Gd-BOPTA, commercially available from MULTIHANCE, Bracco, Rome, Italy. The optimal inversion time was selected to null the left ventricular myocardial signal using a Look-Locker sequence. A free-breathing ECG-triggered navigator-gated inversion-recovery gradient echo imaging sequence was used for all acquisitions. The imaging parameters were TR/TE=5.2/2.6 ms., a flip angle=25°, a field-of-view=320×400×90 mm$^3$, and a spatial resolution=1.4×1.4×4.0 mm$^3$. A respiratory navigator placed on the dome of the RHD was used for respiratory motion compensation, utilizing an end-expiration adaptive gating window strategy with a target efficiency varying between 40 and 50%. Saturation bands were placed over the stationary tissues. All imaging was performed axially with right-left phase-encoding to reduce respiratory artifacts from the chest wall.

The k-space data were exported and transferred to a stand-alone workstation for further analysis, such as the image generating unit 33 and/or the image processing system 40 of FIG. 2. The method of the present invention was implemented in the predetermined software 46 of FIG. 2, for example, using MATLAB v7.6, a mathematical and numerical computing environment implemented as a software application commercially available from MATHWORKS, Natick, Mass., U.S.A.. For all datasets, the motion correction for improved SNR by the present invention was performed independently for each coil of the MRI system shown in FIG. 1. Exemplary numerical values of the parameters for the displacement of the object and/or the heart of the object in the x direction were chosen as $x_{step}$=0.2 pixels, $x_{min}$=−10 pixels, and $x_{max}$=10 pixels. The alternating minimization method for iteratively estimating the translational motion parameters and the phase-corrected estimate for the maximum-likelihood estimation method was performed, for example, for five iterations. Comparison images were generated via the method of the prior art by using only the NAV-accepted data and by discarding and, thus, not using the NAV-rejected data; that is, the k-space rejected data. In all cases, the final images were reconstructed and generated in step 78 of FIG. 3 by a method known in the art, for example, by calculating a root-sum-squares of the individual coil images.

For coronary MRI, objective vessel sharpness and SNR measurements were used to evaluate the reconstructions for all datasets using the present invention and using the methods of the prior art. SNR measurements were performed on the raw images using MATLAB v7.6, a mathematical and numerical computing environment implemented as a software application commercially available from MATHWORKS, Natick, Mass., U.S.A. For coronary MRI, the mean signal intensity of the ascending aorta, at the level that the left main coronary artery branches off, was measured by drawing a region-of-interest (ROI), having approximately a 10 mm radius, for both reconstructions of the present invention and of the prior art. For LA LGE, the mean signal intensity was measured in the LA and right atrium (RA) blood pools. Noise was measured in the non-signal areas of each image using a larger ROI. SNR was calculated as the ratio of the mean signal to the standard deviation of the noise. SNR gain was calculated as the ratio of the SNRs obtained from the method of the present invention along with the image reconstruction method of the prior art. This was compared to the maximum theoretical SNR gain, defined as the theoretical SNR if a given k-space line was acquired ($n_{rej}$+1) times without undergoing any motion, where $n_{rej}$ is the number of times that such a k-space line was rejected due to NAV in the original acquisition. A predetermined software application or tool, known in the art as a "SoapBubble tool" which facilitates visualization and quantitative comparison of 3D volume targeted coronary MRI data, was used to quantitatively evaluate LAD vessel sharpness. Vessel sharpness scores were calculated for both sides of the vessel using a known Deriche algorithm. Final normalized sharpness was defined as the average score of both sides divided by the center of vessel intensity.

Figure 4:
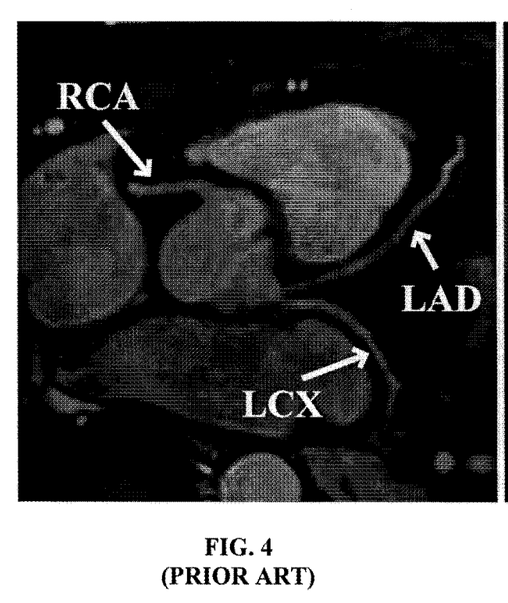
FIG. 4 is a reformatted axial image of left coronaries from a healthy subject, reconstructed using a method of the prior art.
Figure 5:
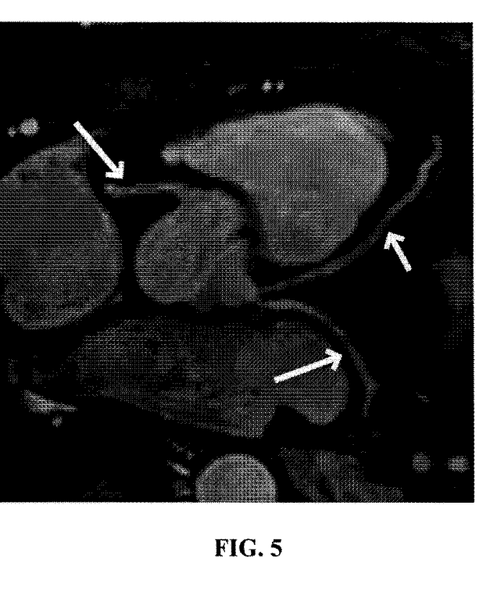
FIG. 5 is a reformatted axial image of left coronaries from a healthy subject, reconstructed using the method of the exemplary embodiment of the present invention.
Figure 6:
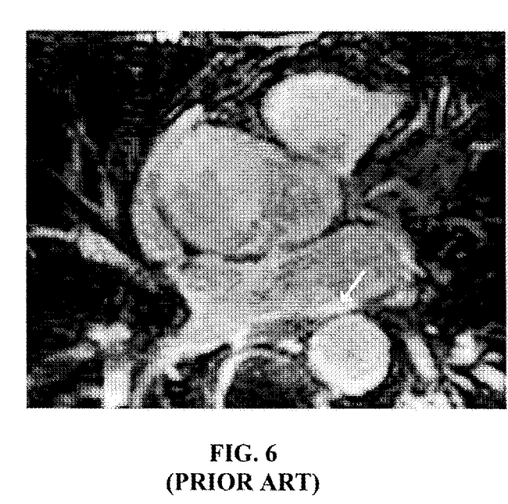
FIG. 6 is an axial slice of left atrium late gadolinium enhancement from a patient who underwent pulmonary vein isolation for treatment of atrial fibrillation, reconstructed using a method of the prior art.

As described in greater detail herein, FIG. 4 is a reformatted axial image of left coronaries from a healthy subject, reconstructed using a method of the prior art; FIG. 5 is a reformatted axial image of left coronaries from a healthy subject, reconstructed using the method of the exemplary embodiment of the present invention; FIG. 6 is an axial slice of left atrium late gadolinium enhancement from a patient who underwent pulmonary vein isolation for treatment of atrial fibrillation, reconstructed using a method of the prior art; and FIG. 7 is an axial slice of left atrium late gadolinium enhancement from a patient who underwent pulmonary vein isolation for treatment of atrial fibrillation, reconstructed using the method of the exemplary embodiment of the present invention.

In a first illustrative example, left coronary MRI and LA LGE imaging were successfully completed in all subjects without complications, with an average gating efficiency of 51.5±8.5% and 42.9±4.7% respectively. FIGS. 4-5 show reformatted axial images or slices of MRI scans of left coronaries from a healthy subject, reconstructed using the method of the prior art, and using the method of the present invention, respectively. FIGS. 4-5 depict the left anterior descending (LAD), left circumflex (LCX) and right coronary artery (RCA) of a healthy subject, indicated by the arrows in FIGS. 4-5, using image reconstruction as in the prior art employing only NAV-accepted data, shown in FIG. 4, and using image reconstruction by the present invention shown in FIG. 5 which employs both the NAV-accepted data and the NAV-rejected data; that is, the accepted k-space lines and the rejected k-space lines, respectively.

As shown in FIGS. 4-5, the images of the coronary arteries are similar in terms of visualization and sharpness, although the method of the present invention has an 11% higher SNR compared to the method of the prior art, due the utilization of the NAV-rejected k-space lines by the present invention.

Figure 7:
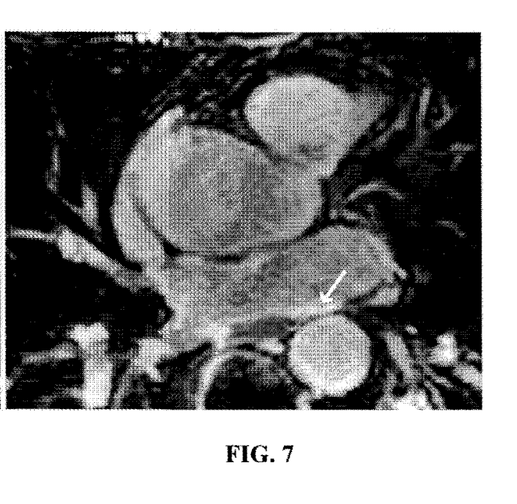
FIG. 7 is an axial slice of left atrium late gadolinium enhancement from a patient who underwent pulmonary vein isolation for treatment of atrial fibrillation, reconstructed using the method of the exemplary embodiment of the present invention.

In a second illustrative example, FIGS. 6-7 show an example axial slice of LA LGE from a patient who underwent PVI for treatment of atrial fibrillation, reconstructed using the method of the prior art with only NAV-accepted data, shown in FIG. 6, and the method of the present invention, as shown in FIG. 7 which employs both the NAV-accepted data and the NAV-rejected data; that is, the accepted k-space lines and the rejected k-space lines, respectively. Both of the respective images in FIGS. 6-7 show the enhancement of the LA wall, as indicated by the arrows in FIGS. 6-7, and are structurally similar, with both images visualized similarly using both of the method of the prior art and the method of the present invention. However, for this patient, the method of the present invention has a 32-39% higher SNR in the LA blood pool, and a 39% higher SNR in the RA blood pool compared to the method of the prior art.

In further illustrative examples, Tables 1-2 list SNR measurements of both the method of the prior art and the method of the present invention.

Tables 1-2 summarize the SNR measurements of the ascending aorta and the corresponding SNR gain, and normalized vessel sharpness measurements for left coronary MRI; as well as the SNR measurements of the LA and the RA, and the respective SNR gains. For the left coronary MRI shown in Table 1, there was a significant difference between the SNR of the method of the present invention compared to the method of the prior art; for example, an SNR of 42.7±10.6 vs. 36.6±10.2, respectively, and P<0.001. However, there was no significant difference in terms of the normalized vessel sharpness, for example, an SNR of 0.455±0.075 vs. 0.463±0.063, respectively, and P=0.19. The SNR gain of the method of the prior art, for example, an SNR gain of 1.17±0.07, and the maximum theoretical SNR gain of, for example, 1.19±0.09, were also not statistically different, with P=0.12. For LA LGE shown in Table 2, there were significant differences in terms of the SNR for the methods of the present invention and of the prior art, measured in both LA, with an SNR of the present invention being of 27.9±14.2 vs. 22.7±11.1 of the prior art, and P<0.001; and RA, with an SNR of the present invention being 31.4±16.1 vs. 25.7±13.2 for the prior art, and P<0.001. The SNR gain of the method of the present invention was 1.21±0.09 as measured in the LA, and an SNR of 1.22±0.09 as measured in the RA, with the maximum theoretical SNR gain of 1.24±0.07 not statistically different, and with P=0.11 and P=0.25 respectively.

TABLE 1

Left Coronary MRI

|  | Vessel Sharpness | SNR | SNR Gain (%) |
|---|---|---|---|
| Present Invention | 0.455 ± 0.075 | 42.7 ± 10.6 | 1.17 ± 0.07 |
| Prior Art | 0.463 ± 0.063 | 36.6 ± 10.2 | 1.00 ± 0.00 |
| P-Value | 0.19 | <0.001 | <0.001 |

TABLE 2

LA LGE

|  | SNR (LA) | SNR Gain (%) | SNR Gain (RA) | SNR Gain (%) |
|---|---|---|---|---|
| Present Invention | 27.9 ± 14.2 | 1.21 ± 0.09 | 31.4 ± 16.1 | 1.22 ± 0.09 |
| Prior Art | 22.7 ± 11.1 | 1.00 ± 0.00 | 25.7 ± 13.2 | 1.00 ± 0.00 |
| P-Value | <0.001 | <0.001 | <0.001 | <0.001 |

Referring to Table 3, a qualitative assessment was also performed for the image quality of the present invention compared to a standard dataset obtained from the method of the prior art, which was also performed for all images. Left coronary MRI and LGE images were written into a Digital Imaging and Communications in Medicine (DICOM) format and imported into VIEWFORUM vR4.2V1L2, a 3D visualization and analysis software application, commercially available from PHILIPS HEALTHCARE, Best, The Netherlands; for qualitative evaluation without reformatting by a "blind reviewer" with over ten years of experience. For coronary MRI, separate scores were given to left main (LM), proximal left anterior descending (LAD), mid LAD, proximal left circumflex (LCX) and proximal right coronary artery (RCA) areas in the images. These scores were then combined for statistical analysis. For LA LGE, subjective scores were given for overall image quality of the axial images. For all images, scores were also given for freedom from motion artifacts. All scores were given on a 4-point scale (1=poor, 2=fair, 3=good, 4=excellent). Additionally, a dichotomous score (yes/no) was noted on the diagnostic quality of the LA LGE images.

Imaging scores, normalized vessel sharpness, and SNR are presented as mean plus or minus one standard deviation. The signed rank test was used for imaging scores to test for the null hypothesis that the central tendency of the difference was zero for the two reconstructions. All statistical analyses were performed using SAS v9.3, a statistical analysis system application software commercially available from the SAS Institute, Cary, N.C., U.S.A. SNR and normalized sharpness scores were compared using the paired t-test. A P value of less than 0.05 was considered to be significant.

Table 3 depicts the qualitative scores for overall image quality and freedom from motion artifacts for left coronary MRI and LA LGE, as well as the presence of enhancement in LA LGE. There were no significant differences between the method of the present invention and the method of the prior art in terms of overall image quality and the presence of motion artifacts for both coronary MRI, with P=0.50 and P=1.00, respectively, and LA LGE with P=1.00 and P=1.00, respectively. Furthermore, there was no significant disagreement between the two methods in terms of detection of enhancement for LA LGE.

TABLE 3

| | Left Coronary MRI | | LA LGE | | |
| --- | --- | --- | --- | --- | --- |
| | Image Score | Freedom from Motion | Image Score | Freedom from Motion | Presence of LGE |
| Present Invention | 2.84 ± 1.13 | 2.90 ± 0.99 | 3.00 ± 0.71 | 3.57 ± 0.60 | 6/21 |
| Prior Art | 2.88 ± 1.08 | 2.90 ± 0.99 | 3.00 ± 0.71 | 3.57 ± 0.60 | 6/21 |
| P-Value | 0.50 | 1.00 | 1.00 | 1.00 | 1.00 |

Accordingly, as shown in Table 3, there is no disadvantage of the present invention by utilizing the motion corrupted data; that is, the rejected k-space data, in conjunction with the accepted k-space data, since the image quality and freedom from motion artifacts are not reduced, and the scan time is not increased, relative to the methods of the prior art, by implementing the present invention.

The present invention, as set forth herein, was evaluated and compared to methods of the prior art, with the present invention providing image reconstruction that is associated with improved SNR compared to such methods of the prior art, in which the present invention uses information from NAV-rejected k-space lines for high-resolution free-breathing MRI acquisitions. These rejected k-space lines are obtained, and then discarded and not used in image reconstruction in the prior art. Thus, the present invention is able to improve the SNR when reconstructing MR images without requiring additional acquisition time, since such rejected k-space lines were already obtained. Furthermore, the present invention does not suffer from additional artifacts or blurriness, which occurs in images reconstructed in the prior art either by failing to compensate for motion of the object using the rejected k-space lines, as in the present invention, or by failing to utilize the entire k-space, including rejected k-space lines and image characteristics represented by such rejected k-space lines, as in the present invention.

The present invention is also advantageous when compensating for motion of the object, and in particular breathing movement of the objects, since there are significant variations in breathing patterns of objects, such as patients or subjects undergoing MRI. Such significant variations are manifested not only in terms of differences in gating efficiency, but also in terms of how many times each line has to be re-acquired when using NAV. For healthy subjects, the maximum number of re-acquisitions is, for example, 26, whereas for the patients such as those with ailments, the number of re-acquisitions goes up to, for example, 61. This difference in the number of times that each k-space line needs to be re-acquired leads to a non-trivial relationship between the SNR gain and the navigating efficiency. Hence, a 50% gating efficiency does not translate to a $\sqrt{}\approx 1.414$ gain in SNR. The variation in the breathing patterns may also result in rejected k-space lines that are well out of the gating window. Image quality may be further improved by only utilizing rejected k-space lines within a larger gating window for NAV; for example, a window of 15 mm., using the present invention. The larger gating window may be retrospectively applied using the NAV data. Regardless of the size of the NAV gating window, the inclusion of all rejected k-space lines by the present invention did not deteriorate the image quality of the reconstructed MR images.

In evaluating the present invention compared to the prior art, the present invention was used in imaging sequences with relatively low SNR. LGE imaging has an inherently low SNR due to the application of an inversion pulse and lack of recovery. Additionally, the presence of gadolinium affects the contrast of the k-space lines acquired over time. Thus, if a line is rejected and re-acquired, the contrast will not be exactly the same due to the changing inversion time and effects of contrast wash-out. This phenomenon may create additional contrast differences between the present invention and methods of the prior art, especially if central k-space lines are rejected and re-acquired over multiple heart cycles, and so the present invention may have further advantages over the methods of the prior art in other imaging circumstances.

Furthermore, the reconstruction time of an exemplary implementation of the present invention, using MATLAB v7.6, a mathematical and numerical computing environment implemented as a software application commercially available from MATHWORKS, Natick, Mass., U.S.A., was approximately 18 ms. per k-space line, although the exact value depends on the number of rejected acquisitions for each k-space line. While such a reconstruction time is not substantial and is only an example of evaluation of the present invention, alternative embodiments of the present invention may also use other known and faster methods for reducing the reconstruction times for each k-space line, due to the typical need for reconstructing multiple coil data for multiple k-space lines per segment. Thus, for real-time reconstruction, alternative reconstruction techniques based on other programming languages or parallel implementations on graphics processing units may be used in the present invention for improved reconstruction times.

In addition, for imaging sequences shown herein for the present invention, saturation bands were used to suppress the signal from stationary tissues, such as arms and the back of the object. Thus, the majority of the signal in each coil comes from the moving objects, and the acquired k-space lines can be corrected for translational motion using the present invention. In cases in which the stationary tissues are not suppressed, these stationary tissues may be segmented out, and their signal contribution may be subtracted out from individual k-space lines before applying motion correction using the present invention. When using segmented acquisitions of high-resolution CMR, the application of saturation bands, as was done in evaluating the present invention, does not increase the scan time, since imaging is usually only performed during the rest period of the heart cycle.

In the prior art, SNR increases for both coronary MRI and LGE have been reported when imaging at higher magnetic fields. While SNR increases between 30%-60% have been reported in the prior art, further SNR increases may be provided by the present invention. Accordingly, in alternative embodiments of the present invention, the present invention may be combined with known methods of the prior art, such as higher magnetic fields to obtain further increases in SNR, so that it may be possible to use the improved SNR of the present invention with other known SNR improvement methods for higher spatial resolution in MRI.

As described herein, the present invention is advantageous over the prior art, in that, in combination with a respiratory motion correction method based on maximum-likelihood estimation, the rejected k-space lines, which have hitherto been discarded in the prior art, are instead used in the present invention to create estimated parameters in conjunction with the accepted k-space lines to improve the SNR during image reconstruction without prolonging the scan time. Such information represented by the rejected k-space lines, although obtained and available but discarded in the prior art, are instead used in the present invention for improving a fundamental property of an imaging protocol, which is the signal-to-noise ratio. The performance and image quality gains achieved by the present invention are similar to those gains achieved by using a stronger magnet in the MRI apparatus, which are implemented in the prior art at considerably greater cost and fabrication complexity, or by averaging for a longer duration, which increases the image processing time in the prior art methods.

In addition, the present invention may be implemented in hardware and/or software, for example, in the image generating unit 33 of FIG. 1 and/or the processor 42 using the predetermined software 46 in FIG. 2, and so the present invention may be used in any known MRI apparatus, such as known MRI scanners as well as MRI scanners in the prior art for generating images with improved SNR. Furthermore, an MR image using the methods of the prior art can also be generated in parallel with processing by the present invention, since the present invention and the prior art methods share the same k-space data, and so the present invention may be used as an option to the prior art methods at no added cost in terms of object scanning and data acquisition times, since the present invention does not require additional scanning or data acquisition. Since the k-space data rejected by the respiratory navigator, or NAV, have already been obtained when obtaining the full set of k-space data, so the present invention does not prolong scan time of the MRI apparatus.

Moreover, such image reconstruction in the prior art is done by just using the k-space data accepted by the respiratory navigator, whereas such rejected k-space data, which may be lying outside the pre-specified respiratory gating window, are discarded in the prior art. By using the rejected k-space data, instead of discarding such data as in the prior art, the image reconstruction by the present invention improves the signal-to-noise ratio when reconstructing the images, which may improve the diagnostic ability of the reconstructed images in low SNR applications, such as in viability studies.

In addition, the present invention may also perform k-space location-dependent motion correction, in which different motion correction techniques described herein as well as techniques known in the art are applied to different parts of the k-space. Since different regions of k-space carry different types of information about the imaged object, the requirements for accuracy of a motion correction technique may be different for each region. For example, the center of k-space requires very accurate motion correction, and therefore a highly accurate motion measurement and compensation technique is needed for this region for optimal imaging and motion correction, while processing of the outer k-space for motion correction does not require such processing for highly accurate motion measurement and compensation. In another example, in 3D imaging, different ky–kz regions can have different motion correction schemes applied to each region. For example, the center of k-space can be acquired using a prolonged breath-hold by the patient, while the outer region of k-space can be acquired during free-breathing by the patient or using navigator technology with a very large gating window to increase data acquisition efficiency. In another embodiment, navigator bellows known in the art can be used for the data processing and the motion correction of the outer k-space, while a diaphragmatic navigator can be used for the data processing and the motion correction of the inner k-space. To allow such use of different equipment and data acquisition methods such as navigator bellows and a diaphragmatic navigator, one may need to use different profile ordering of the k-space to take into account motion in different regions of the k-space in addition to any use of contrast agents.

Additional applications of the present invention are not limited to MRI applications for cardiac and cardiovascular diagnoses. For example, the present invention may be extended to compensate for respiratory motion effects by using motion-corrupted data when performing MRI on the liver or other portions of the body, including the cranial region, which may be affected by respiratory motion or other typical movement of a subject. Furthermore, the present invention may also be applied to any image reconstruction method in the prior art which involves the discarding of corrupted image data, such as by motion artifacts and effects, in that the present invention would not discard such corrupted image data, but instead would use the corrupted image data, as described herein, to perform motion compensation in order to obtain highly accurate image reconstruction despite such motion artifacts and effects.

Accordingly, the present invention has many advantages, such as not requiring additional information on a free-breathing scan, and does not prolong the scan time, but instead reduces the apparent noise level for improved SNR and better diagnostic functionality.

The above-described apparatus and methods according to the present invention can be implemented in hardware, firmware or as software or computer code that can be stored in a recording medium such as a CD ROM, a RAM, a ROM, a floppy disk, DVDs, a hard disk, a magnetic storage media, an optical recording media, or a magneto-optical disk or computer code downloaded over a network originally stored on a remote recording medium, a computer readable recording medium, or a non-transitory machine readable medium and to be stored on a local recording medium, so that the methods described herein can be rendered in such software that is stored on the recording medium using a general purpose computer, a digital computer, or a special processor or in programmable or dedicated hardware, such as an ASIC or FPGA. As would be understood in the art, the computer, the processor, microprocessor controller or the programmable hardware include memory components, e.g., RAM, ROM, Flash, etc. that may store or receive software or computer code that when accessed and executed by the computer, processor or hardware implement the processing methods described herein. In addition, it would be recognized that when a general purpose computer accesses code for implementing the processing shown herein, the execution of the code transforms the general purpose computer into a special purpose computer for executing the processing shown herein.

While the preferred embodiments of the present invention have been illustrated and described, it will be understood by those skilled in the art that various changes and modifications may be made, and equivalents may be substituted for elements thereof without departing from the true scope of the present invention. In addition, many modifications may be made to adapt to a particular situation and the teaching of the present invention without departing from the central scope. Therefore, it is intended that the present invention not be limited to the particular embodiment disclosed as the best mode contemplated for carrying out the present invention, but that the present invention include all embodiments falling within the scope of the appended claims.

What is claimed is:

1. An apparatus for processing image data, the apparatus comprising:
   a processor, operating predetermined software, for receiving the image data of a subject from a data source, for classifying the received image data as accepted image data or rejected image data, and for applying a predetermined relationship between the accepted image data and the rejected image data to correct for motion of the subject and to generate a reconstructed image of the subject corrected for the motion from the image data; and
   an output device for outputting the reconstructed image.

2. The apparatus of claim 1, wherein the image data corresponds to at least one of cardiac data, cardiovascular data, coronary arterial data, and pulmonary vein data in the subject.

3. The apparatus of claim 1, further comprising:
   a magnetic resonance image (MRI) system for obtaining the image data of the subject.

4. The apparatus of claim 1, wherein the processor classifies the received image data using a predetermined navigator method.

5. The apparatus of claim 1, wherein the processor classifies the received image data into accepted k-space data and rejected k-space data as the accepted image data and the rejected image data, respectively.

6. The apparatus of claim 1, wherein the processor applies the predetermined relationship using a maximum-likelihood method to estimate at least one of a translational motion parameter and a phase-corrected estimate to correct for the motion of the subject.

7. The apparatus of claim 6, wherein the processor uses an alternating minimization method to iteratively estimate the at least one of a translational motion parameter and a phase-corrected estimate.

8. The apparatus of claim 1, wherein the processor generates the reconstructed image of the subject with a relatively high signal-to-noise ratio.

9. An apparatus for processing magnetic resonance image (MRI) data, the apparatus comprising:
   a processor, operating predetermined software, for acquiring k-space data from an image data that is generated based on MRI data, for classifying the acquired k-space data as accepted k-space data or rejected k-space data, and for applying a predetermined relationship between the accepted k-space data and the rejected k-space data to correct for motion of a subject and to generate a reconstructed image of the subject corrected for the motion from the image data; and
   an output device for outputting the reconstructed image.

10. The apparatus of claim 9, wherein the image data corresponds to at least one of cardiac data, cardiovascular data, coronary arterial data, and pulmonary vein data in the subject.

11. The apparatus of claim 9, further comprising:
    a magnetic resonance image (MRI) system for obtaining the image data of the subject.

12. The apparatus of claim 9, wherein the processor classifies the received image data using a predetermined navigator method.

13. The apparatus of claim 9, wherein the processor applies the predetermined relationship using a maximum-likelihood method to estimate at least one of a translational motion parameter and a phase-corrected estimate to correct for the motion of the subject.

14. The apparatus of claim 13, wherein the processor uses an alternating minimization method to iteratively estimate the at least one of a translational motion parameter and a phase-corrected estimate.

15. The apparatus of claim 9, wherein the processor generates the reconstructed image of the subject with a relatively high signal-to-noise ratio.

16. A method for processing image data, the method comprising:
    receiving the image data of a subject from a data source;
    classifying the received image data as accepted image data or rejected image data;
    operating a predetermined software using a processor for applying a predetermined relationship between the accepted image data and the rejected image data to correct for motion of the subject;
    generate a reconstructed image of the subject from the image data, with the reconstructed image being corrected for the motion of the subject; and
    outputting the reconstructed image from an output device.

17. The method of claim 16, wherein the image data corresponds to at least one of cardiac data, cardiovascular data, coronary arterial data, and pulmonary vein data in the subject.

18. The method of claim 16, wherein the receiving includes:
    receiving the image data of the subject from a magnetic resonance image (MRI) system as the data source.

19. The method of claim 16, wherein the classifying includes:
    classifying the received image data using a predetermined navigator method.

20. The method of claim 16, wherein the classifying includes:
    classifying the received image data into accepted k-space data and rejected k-space data as the accepted image data and the rejected image data, respectively.

21. The method of claim 16, wherein applying the predetermined relationship includes:
    using a maximum-likelihood method with the predetermined relationship to estimate at least one of a translational motion parameter and a phase-corrected estimate to correct for the motion of the subject.

22. The method of claim 21, wherein the applying includes:
    iteratively estimating the at least one of a translational motion parameter and a phase-corrected estimate.

23. The method of claim 16, wherein the generating includes:
    generating the reconstructed image of the subject with a relatively high signal-to-noise ratio.

* * * * *